United States Patent [19]

Haslam et al.

[11] Patent Number: 4,478,822

[45] Date of Patent: Oct. 23, 1984

[54] DRUG DELIVERY SYSTEM UTILIZING THERMOSETTING GELS

[75] Inventors: John L. Haslam; Takeru Higuchi; Arthur R. Mlodozeniec, all of Lawrence, Kans.

[73] Assignee: Merck & Co., Inc., Rahway, N.J.

[21] Appl. No.: 495,239

[22] Filed: May 16, 1983

[51] Int. Cl.³ .................. A61K 31/74; A61K 31/70; A61K 31/135; A61K 31/54; A61K 31/415; A61K 31/435; A61K 31/19; A61K 31/66
[52] U.S. Cl. .................................. 424/78; 424/285; 424/300; 424/85; 424/309; 424/311; 424/94; 424/313; 424/317; 424/114; 424/321; 424/322; 424/116; 424/324; 424/326; 424/177; 424/330; 424/343; 424/180; 424/181; 424/209; 424/211; 424/220; 424/221; 424/224; 424/230; 424/238; 424/243; 424/246; 424/248.51; 424/251; 424/253; 424/254; 424/256; 424/258; 424/263; 424/265; 424/267; 424/270; 424/271; 424/273 P; 424/273 R; 424/274; 424/275; 424/283

[58] Field of Search .................. 424/78, 85, 94, 177, 424/180, 181, 209, 211, 220, 221, 224, 230, 238, 243, 246, 248.51, 251, 253, 254, 256, 258, 263, 265, 267, 270, 271, 273 P, 273 R, 274, 275, 283, 285, 300, 309, 311, 313, 317, 321, 322, 324, 326, 330, 343

[56] References Cited

U.S. PATENT DOCUMENTS 2,979,528  4/1961  Lundsted ........................... 260/584
4,188,373  2/1980  Krezanoski ........................ 424/177

FOREIGN PATENT DOCUMENTS 1072413  7/1976  Canada .

OTHER PUBLICATIONS

Journal of Pharm. & Pharmacology—"Novel Poloxamer & Poloxamine Hydrogels: Swelling & Drug Release" vol. 32, p. 5P (1980) by, A. Saden, A. J. Florence, T. L. Whateley.

Primary Examiner—Douglas W. Robinson
Attorney, Agent, or Firm—Manfred Polk; Michael C. Sudol, Jr.

[57] ABSTRACT

This invention relates to a unique drug delivery system for delivering drugs to a body cavity. The drug delivery system comprises a medicament and a polymer such that the drug delivery system is a liquid at room temperature but forms a semi-solid or gel at the body temperature in the body cavity.

55 Claims, 1 Drawing Figure

DRUG DELIVERY SYSTEM UTILIZING THERMOSETTING GELS

BACKGROUND OF THE INVENTION

A goal of pharmaceutics is to efficiently deliver a therapeutic drug to the site of action. Over the years methods have been developed to achieve this goal.

One approach to the drug delivery improvement is to use a formulation which is liquid at room temperature but which forms a semi-solid when warmed to body temperature.

Such a system hs been described in U.S. Pat. No. 4,188,373 using "Pluronic ® polyols" as the thermally gelling polymer. In this system the concentration of polymer is adjusted to give the desired sol-gel transition temperature, that is the lower concentration of polymer gives a higher sol-gel transition temperature. However, with the currently commercially available "Pluronic ®" polymers the ability to obtain a gel of the desired rigidity is limited while maintaining the desired sol-gel transition temperature at physiologically useful temperature ranges near 26°-35° C.

Similarly a Canadian patent 1,072,413 which relates to (poloxamer polyols) with gelling temperatures higher than room temperature uses additives to bring about the gelling characteristics of the polymer which contains therapeutic or other type agents. Also in this Canadian patent "Tetronic ®" polymers are used as additive agents rather than the primary polymeric agent as in the instant case.

SUMMARY OF THE INVENTION

The present invention provides a pharmaceutical vehicle which is useful in delivering pharmacologically active medicaments to a body orifice such as the rectum, vagina, urethra, external auditory meatus, nasal passage or buccal or oral cavity. The drug delivery system consists of a clear physiologically acceptable liquid which forms semi-solid "gel" at human body temperature. The sol-gel transition temperature and rigidity of the gel can be modified by changes in polymer concentration combined with the pH and ionic strength of the solution.

We describe here a unique drug delivery system which at room temperature has the properties of a liquid, but when administered rectally, nasally, vaginally or otically or to the oral cavity, buccal pouch or urethral lumen, changes to a semi-solid or gel when warmed by the body. The advantages of such a system are: the convenience of handling a liquid during the administration phase including the property of a liquid to make intimate contact before gel formation. Once gelled the advantage is the prolonged time of release of the drug at the site of administration. The advantage of increasing the release time results not only in a prolonged time of therapeutic effectiveness but as a result of enhanced delivery the dose of drug can be reduced. The gelling characteristics of this system also enhance the retention of product formulations within body cavities or lumens which might normally be rapidly depleted if dosed exclusively as liquids. The dose sparing ability of such a drug delivery system is realized when serious side effects of some drugs are reduced.

It has been discovered that certain polymers are useful vehicles having the properties set forth above. The polymers are tetra substituted derivatives of ethylene diamine (poloxamine, w=2 in Formula I), propylene diamine (w=3), butylenediamine (w=4), pentylenediamine (w=5) or hexylene diamine (w=6). The substituents are block copolymers of poly(oxypropylene) and poly(oxyethylene) of various chain lengths and ratios x to y in the general formula of the polymer shown below.

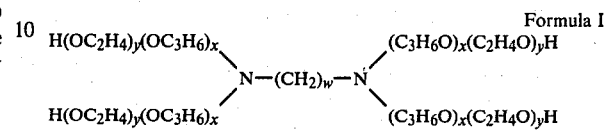

Formula I wherein w is an integer from 2 through 6.

A typical polymer system of our invention would contain a polymer containing approximately 40 to 80% poly(oxyethylene) and approximately 20 to 60% poly(oxypropylene). The total molecular weight of the polymer used in our invention is greater than 7,000 and can go as high as 50,000 but preferably is in the range of 7,000 to 30,000, and x and y are any integers within the above constraints. Preferred polymers are those of the formula above wherein w=2, namely the poloxamine polymers.

The aqueous drug delivery vehicle would contain from 10% to 50% by weight of the entire vehicle of polymer described above. The aqueous drug delivery vehicle would also contain the drug or therapeutic agent in addition to various additives such as acids or bases to adjust the pH of the composition, buffers to maintain the pH, preservatives to control bacterial contamination, other additives to provide for drug solubility and stability and formulation performance with purified water making up the remainder of the drug delivery vehicle.

DETAILED DESCRIPTION OF THE INVENTION

Figure 1:
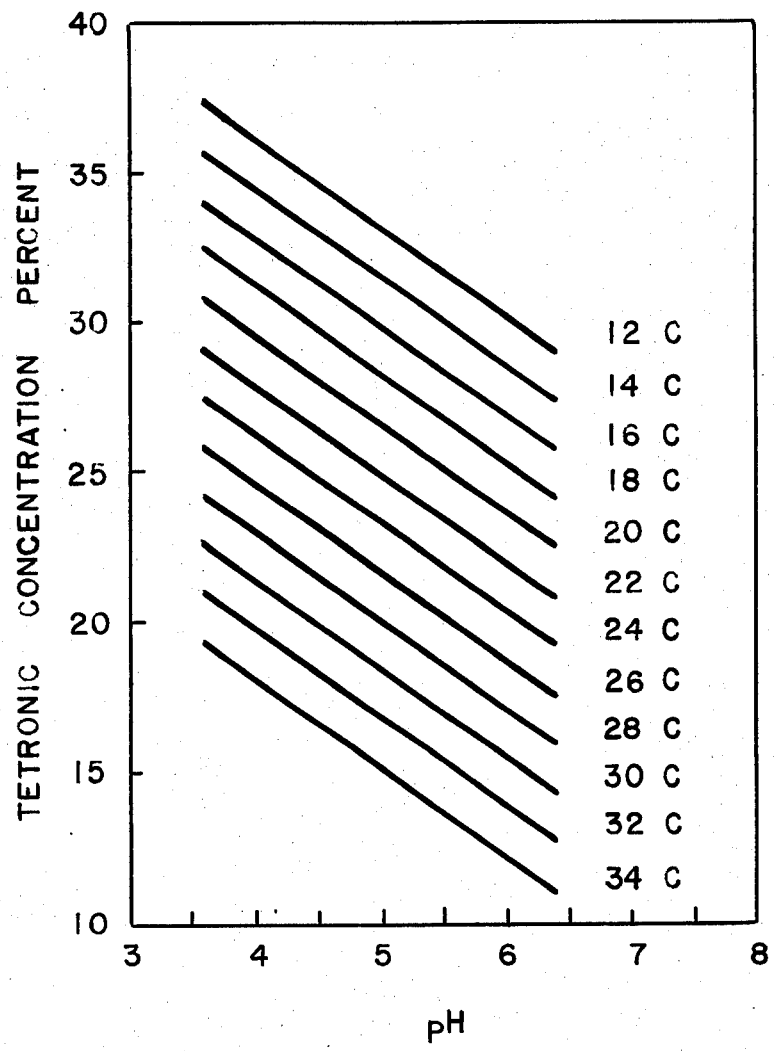

The invention consists of a pharmaceutical composition or drug delivery system which is a clear physiological acceptable solution at room temperature or lower but which forms a semi-solid or gel when warmed to body temperature. The unique feature of this system is that both the gel transition temperature and/or the rigidity of the gel can be modified by adjustment of the pH and or ionic strength and polymer concentration.

The ability to change the sol-gel transition temperature by pH adjustment is a critical feature of the invention which overcomes many of the disadvantages of previous approaches. Also the sol-gel transition temperature can be modified somewhat by ionic strength adjustment.

An example of a drug delivery vehicle in accordance with this invention consists of an aqueous solution of, for example, a tetra substituted ethylene diamine block copolymer of poly(oxyethylene)-poly(oxypropylene) (where w=2 in Formula I) in which the substitution at the nitrogen is to the poly(oxypropylene) block and the polymer consists of about 40-80% as the poly(oxyethylene) unit and about 20-60% as the polypropylene unit and which has a total average molecular weight of 7,000 to 50,000 with a preferred range of 7,000-30,000. Such polymers are included in the polymers sold under the trademark "Tetronic ®" polyols by BASF Wyandotte Corporation.

Other polymers where w=3 to 6 (of Formula I) can be made according to methods known in the art (Block and Graft Copolymerization, Vol. 2 edited by R. J. Ceresa published by John Wiley and Sons, 1976) by using the appropriate initiators such as for example propylenediamine, butylenediamine, pentylenediamine and hexylenediamine.

The preferred polymers are those which form gels at a concentration range of 10 to 50% of the polymer to water.

A good example of a typical polymer used in the drug delivery system of our invention is Tetronic ®1307 which thermally gels over a concentration range of about 15 to 35% in water with gelling temperatures of about 30° to 10° C. at neutral pH. The gel strength at 35% is much more rigid than the 15% gel. However, with a sol-gel transition temperature of about 10° C. any useful liquid product would have to be refrigerated below this temperature. A useful vehicle can be prepared however by modification of both concentration and pH. For example a 27% Tetronic ®1307 solution at neutral pH has a sol-gel transition temperature of about 16° C. but at pH 4 (adjusted to such with HCl at 10° C.) the transition temperature is about 25° C. The gel formed under these conditions meets the requirements of a fairly rigid gel which is a liquid at room temperature.

The effect of pH and polymer concentration on gelling temperature for Tetronic ®1307 is shown in FIG. 1. Thus, for example, at a concentration of polymer to water of 25% the gelling temperature is 19° C. at pH 6 and increases to 26° C. at pH 4.

For administration of the drug delivery system of our invention to the rectum, urethra, nasal cavity, vagina, auditory meatis, oral cavity or buccal pouch as a liquid the pH of the system can range from 2 to 9 with the preferred pH range being 4 to 8. The pH, concentration and gelling temperatures will vary for any individual polymer falling within the class covered in this invention and these factors can be determined by those skilled in the art in possession of this concept.

The pH of the drug delivery system is adjusted by adding the appropriate amount of a pharmaceutically acceptable acid or base to obtain the required pH. The acid or base can be any that are known to persons skilled in the art but are preferably hydrochloric acid or sodium hydroxide.

In general the drug delivery vehicle of the present invention will contain from about 0.01 to about 5% of the medicament or pharmaceutical, from about 10 to about 50% of the polymer and from 90 to about 45% water. In special situations, however, the amounts may be varied to increase or decrease the dosage schedule.

If desired, the drug delivery vehicle may also contain, in addition to the medicament, buffering agents and preservatives. Suitable water soluble preservatives which may be employed in the drug delivery vehicle are sodium bisulfite, sodium thiosulfate, ascorbate, benzalkonium chloride, chlorobutanol, thimerosal, phenylmercuric borate, parabens, benzylalcohol and phenylethanol. These agents may be present in amounts of from 0.001 to 5% by weight and preferably 0.01 to 2%. Suitable water soluble buffering agents are alkali or alkali earth carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4-8. As such the buffering agent can be as much as 5% on a weight to weight basis of the total composition.

Another factor which can affect the gelling temperature of the drug delivery vehicle or pharmaceutical composition is the ionic strength and this is done by adding a pharmaceutically acceptable salt, such as sodium chloride, potassium chloride or mixtures thereof or even suitable alkali metal salts such as sodium sulfate and the like. The effect of adding sodium chloride is to decrease the gelling temperature by about 3° C. for a change of 0.2 molar in ionic strength. Under most conditions of use the body's pH and ionic strength will help maintain the drug delivery system as a gel in the rectum, nasal cavity, vagina or auditory meatus.

Any pharmaceutically active material may be delivered in the drug delivery system of this invention. Preferably the drug or pharmaceutical is water soluble although some drugs will show greater solubility in the polymer system than others. Also the drugs may be insoluble and can be suspended in the polymer vehicle.

Suitable drugs which can be administered in, the drug polymer delivery system of the present invention are antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fludalanine/pentizidone; nitrofurazones, and the like; antihistaminics and decongestants such as pyrilamine, cholpheniramine, tetrahydrazoline, antazoline, and the like; anti-inflammatories such as cortisone, hydrocortisone, beta-methasone, dexamethasone, fluocortolone, prednisolone, triamcinolone, indomethacin, sulindac, its salts and its corresponding sulfide, and the like. Also included are antiparasitic compounds such as ivermectin; antiviral effective compounds such as acyclovir and interferon.

For otic use besides the antibacterials and anti-inflammatory drugs the use of local anesthetic is helpful in reducing the pain. Local anesthetics such as benzocaine, lidocaine, procaine and the like can be used.

For treatment of vaginal and urethral conditions requiring antifungal, amebecidal, trichomonacidal agent or antiprotozoals the following can be used such as polyoxyethylene nonylphenol, alkylaryl sulfonate, oxyquinoline sulfate, miconazole nitrate, sulfanilamide, candicidin, sulfisoxazole, nystatin, clotrimazole, metronidazole and the like and for antiprotozoals, chloramphenicol, chloroquine, trimethoprim, sulfamethoxazole and the like.

For use rectally the following suitable drugs can be administered by the drug polymer delivery system of the present invention:

(1) Analgesics such as aspirin, acetaminophen, deflunisal and the like;

(2) anesthetics such as lidocaine, procaine, benzocaine, xylocaine and the like;

(3) antiarthritics such as phenylbutazone, indomethacin, sulindac, dexamethasone, ibuprofen, allopurinol, oxyphenbutazone probenecid and the like;

(4) antiasthma drugs such as theophylline, ephedrine, beclomethasone dipropionate, epinephrine and the like;

(5) urinary tract disinfectives such as sulfamethoxazole, trimethoprim, nitrofurantoin, norfloxicin and the like;

(6) anticoagulants such as heparin, bishydroxy coumarin, warfarin and the like;

(7) anticonvulsants such as diphenylhydantoin, diazepam and the like;

(8) antidepressants such as amitriptyline, chlordiazepoxide, perphenazine, protriptyline, imipramine, doxepin and the like;

(9) antidiabetics such as insulin, tolbutamide, tolazamide, acetohexamide, chlorpropamide and the like

(10) antineoplastics such as adriamycin, flurouracil, methotrexate, asparaginase and the like;

(11) antipsychotics such as prochlorperazine, lithium carbonate, lithium citrate, thioridazine, molindone, fluphenazine, trifluoperazine, perphenazine, amitriptyline, triflupromazine and the like;

(12) antihypertensive such as spironolactone, methyldopa, hydralazine, clonidine, chlorothiazide, deserpidine, timolol, propranolol, metoprolol, prazosin hydrochloride, reserpine and the like; and

(13) muscle relaxants such as melphalan, danbrolene, cyclobenzaprine, methocarbamol, diazepam and the like.

(14) antiprotozoals such as chloramphenicol, chloroquine, trimethoprim and sulfamethoxazole.

Typically as stated previously, the present liquid drug delivery device would contain from about 0.001 to about 5% of the medicament of pharmaceutical on a weight to weight basis. Thus, from one gram of the liquid composition which is about 1 ml of solution, one would obtain about 0.1 mg to about 50 mg of drug.

The particular drug used in the pharmaceutical composition of this invention is the type which a patient would require for pharmacological treatment of the condition from which said patient is suffering. For example, if the patient is suffering from pain or itch of the external auditory canal, the drug of choice would probably be benzocaine.

Also included in this invention is the use of the drug delivery device or pharmaceutical composition minus the active drug or medicament for restoration or maintenance of vaginal acidity. All the ratios of components as described above would be satisfactory for this composition. For this use one would administer the vehicle as needed at the desired pH.

The preparation of the drug delivery systems are described below and the appropriate examples which follow were all carried out according to this procedure. Since the Tetronic ® polymer systems of this invention dissolve better at reduced temperatures, the preferred methods of solubilization are to add the required amount of polymer to the amount of water to be used. Generally, after wetting the polymer by shaking, the mixture is capped and placed in a cold chamber or in a thermostated container at about 0° C. to 10° C. to dissolve the polymer. The mixture can be stirred or shaken to bring about a more rapid solution of the polymer.

The drug substance and various additives such as buffers, salts and preservatives are then added and dissolved. The final desired pH adjustment can be made by adding the appropriate acids or bases such as hydrochloric acid or sodium hydroxide.

When used to treat conditions of the ear or nose the pharmaceutical composition will be administered as a liquid by any conventional means of delivering drop formulations such as by means of an eye-dropper or by using a squeeze bottle such as an Ocumeter ®.

When used to deliver drugs rectally, urethrally or vaginally, the pharmaceutical composition will be administered as a liquid by use of an appropriate syringe adapted with the appropriate delivery tube or needle.

EXAMPLES

The following examples are illustrations and are not intended to be restricive of the scope of the invention.

All percentages are given in (w/w)% and all pH measurements are for 10° C.

EXAMPLE 1

The use of the polymer vehicle to deliver norfloxacin a broad spectrum antimicrobial compound.

|  | Solution 1 | Solution 2 | Solution 3 |
| --- | --- | --- | --- |
| norfloxacin | 0.1% | 0.1% | 0.1% |
| Tetronic ® 1307 | 22.0% | 27.0% | 32.0% |
| pH adjusted with HCl to | 4 | 4 | 4 |
| sufficient purified water to make | 100% | 100% | 100% |
| gel-sol transition temp. | 30° C. | 26° C. | 21° C. |

All three solutions can be administered as described previously as liquids, however, solution 3 would require cooling to below 21° C. before use.

EXAMPLE 2

| Dexamethasone | 0.05% |
| --- | --- |
| Tetronic ® 1307 | 30.0% |
| Benzalkonium chloride | 0.02% |
| pH adjusted with HCl to 4 | |
| sufficient purified water to make | 100% |
| gel-sol transition temperature | 21° C. |

EXAMPLE 3

| Gentamycin sulfate | 0.1% |
| --- | --- |
| Tetronic ® 1307 | 25.0% |
| Benzalkonium chloride | 0.01% |
| Sodium chloride | 0.05% |
| pH adjusted with HCl to 4 | |
| sufficient purified water to make | 100% |
| gel-sol transition temperature | 26° C. |

EXAMPLE 4

| Chloramphenicol | 0.5% |
| --- | --- |
| Tetronic ® 1508 | 20.0% |
| Sodium acetate | 0.3% |
| Benzalkonium chloride | 0.01% |
| pH adjusted with HCl to 5 | |
| sufficient purified water to make gel-sol transition temperature | 100% 27° C. |

EXAMPLE 5

| Lidocaine | 5% |
| --- | --- |
| Tetronic ® 1307 | 25% |
| Benzalkonium chloride | 0.01% |
| pH adjusted with HCl to 4 | |
| Sufficient purified water to make gel-sol transition temperature | 100% 32° C. |

EXAMPLE 6

| Sodium acetate | 2% |
|---|---|
| Tetronic ® 1307 | 21% |
| Benzalkonium chloride | 0.01% |
| pH adjusted with HCl to 5 | |
| sufficient purified water to | 100% |
| gel-sol transition temperature | 25° C. |

EXAMPLE 7

| | Solution 1 | Solution 2 |
|---|---|---|
| Timolol maleate | 0.68% | 0.68% |
| Tetronic ® 1307 | 22% | 27% |
| pH adjusted with HCl to | 4 | 4 |
| sufficient purified water | 100% | 100% |
| gel-sol transition temperature | 30° C. | 26° C. |

If the pharmaceutical compositions of Example 1-7 were compared with similar compositions but without the polymer, it would be expected that the compositions of Examples 1-7 would result in greater sustained concentrations of the drug at the site of administration.

Following the procedure of Examples 1-7 one can use an appropriate amount of the polymers listed below in place of the Tetronic ®1307 or Tetronic ®1508 polymer used in Examples 1-7.

Tetronic 1107
Tetronic 908
Tetronic 707

Following the procedure of Examples 1-7 one can use an appropriate amount of the drugs previously enumerated in this application.

What is claimed is:

1. An aqueous pharmaceutical composition for rectal, urethral, nasal, vaginal, optical or oral in the buccal pouch administration to a body cavity to treat a condition requiring pharmacological treatment comprising a. 10% to 50% by weight of a polymer of the formula:

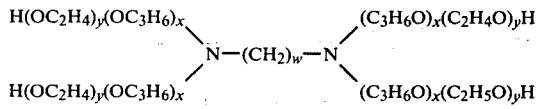

wherein w is an integer of from 2-6 containing approximately 40% to 80% poly(oxyethylene) and approximately 20 to 60% poly(oxypropylene) and having a molecular weight of 7,000 to 50,000; and x and y are any integers within the above constraints; and b. a pharmacologically effective amount of drug selected from the group consisting of anti-bacterial substances, antihistamines and decongestants, anti-inflammatories, anti-parasitics, antiviral, local anesthetics, antifungal, amebecidal, or trichomonocidal agents, analgesics, antiarthritics, antiasthmatics, anticoagulants, anticonvulsants, antidepressants, antidiabetics, antineoplastics, antipsychotics, antihypertensives, and muscle relaxants and anti-protozoals; and c. a pharmaceutically acceptable acid or base being in sufficient quantity to adjust the pH of the composition to range from 2 to 9 and wherein the composition is liquid at about room temperature or below.

2. The composition of claim 1 wherein the polymer is one wherein w is 2.

3. The composition of claim 1 wherein the polymer is Tetronic ®1307.

4. The composition of claim 1 wherein the gel-sol transition temperature of the composition is room temperature or below and said composition is liquid at this temperature.

5. The composition of claim 1 wherein the antibacterial substances are selected from the group consisting of beta-lactam antibiotics, tetracyclines, chloramphenicol, neomycin, gramicidin, bacitracin, sulfonamides, aminoglycoside antibiotics, tobramycin, nitrofurazone, nalidixic acid and analogs and the antimicrobial combination of fludalanine/pentizidone.

6. The composition of claim 1 wherein the antihistaminics and decongestants are selected from the group consisting of perilamine, chlorpheneramine, tetrahydrozaline and antazoline.

7. The composition of claim 1 wherein the anti-inflammatory drugs are selected from the group consisting of cortisone, hydrocortisone, betamethasone, dexamethasone, fluocortolone, prednisolone, triamcinolone, indomethacin, sulindac and its salts and corresponding sulfide.

8. A composition of claim 1 wherein the antiparasitic compound is ivermectin.

9. The composition of claim 1 wherein the antiviral effective compounds are selected from the group consisting of acyclovir and interferon.

10. A composition of claim 1 wherein the local anesthetics are selected from the group consisting of benzocaine, lidocaine and procaine.

11. The composition of claim 1 wherein the antifungal, antiprotozoal, amebecidal or trichomonacidal agent is selected from the group consisting of polyoxyethylene nonylphenol, alkylaryl sulfonate, oxyquinoline sulfate, miconazole nitrate, sulfanilamide, condicidin, sulfisoxazole, nystatin, chlotrimazole, metronidazole, chloramphenicol, chloroquine, trimethoprim or sulfamethoxazole.

12. The composition of claim 1 wherein the analgesic drug is selected from the group consisting of diflunisal, aspirin or acetaminophen.

13. The composition of claim 1 wherein the antiarthritics are selected from the group consisting of phenylbutazone, indomethacin, sulindac, dexamethasone, ibuprofen, allopurinol, oxyphenbutazone or probenecid.

14. The composition of claim 1 wherein the antiasthma drugs are selected from the group consisting of theophylline, ephedrine, beclomethasone diproprionate and epinephrine.

15. The composition of claim 1 wherein the anticoagulants are selected from the group consisting of heparin, bishydroxycoumarin, and warfarin.

16. The composition of claim 1 wherein the anticonvulsants are selected from the group consisting of diphenylhydantoin and diazepam.

17. The composition of claim 1 wherein the antidepressants are selected from the group consisting of amitriptyline, chlordiazepoxide perphenazine, protriptyline, imipramine and doxepin.

18. The composition of claim 1 wherein the antidiabetics are selected from the group consisting of insulin, tolbutamide, tolazamide, acetohexamide and chlorpropamide.

19. The composition of claim 1 wherein the antineoplastics are selected from the group consisting of adriamycin, flurouracil, methotrexate and asparaginase.

20. The composition of claim 1 wherein the antipsychotics are selected from the group consisting of prochlorperazine lithium carbonate, lithium citrate, thioridazine, molindone, fluphenazine, trifluoperazine, perphenazine, amitriptyline and triflupromazine.

21. The composition of claim 1 wherein the antihypertensives are selected from the group consisting of spironolactone, methyldopa, hydralazine, clonidine, chlorothiazide, deserpidine, timolol, propranolol, metoprolol, prazosin hydrochloride and reserpine.

22. The composition of claim 1 wherein the muscle relaxants are selected from the group consisting of melphalan, danbrolene, cyclobenzoprine, methocarbamol and diazepam.

23. The composition of claim 1 which includes a buffering agent or salt of from 0 to 5% by weight of the composition.

24. The composition of claim 23 wherein the buffering agent or salt is selected from the group consisting of alkali or alkali earth carbonates, chlorides, sulfates, phosphates, bicarbonates, citrates, borates, acetates and succinates.

25. The composition of claim 1 which includes from 0.001% to 5% by weight of the composition of a preservative.

26. The composition of claim 25 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

27. The composition of claim 1 wherein the acid or base is selected from the group consisting of hydrochloric acid or sodium hydroxide.

28. A method of treating a condition requiring pharmacological treatment which comprises administering rectal, urethral, nasal, vaginal, optical or oral in the buccal pourch to a body cavity a liquid drug delivery device comprising:

a. 10% to 50% by weight of a polymer of the formula

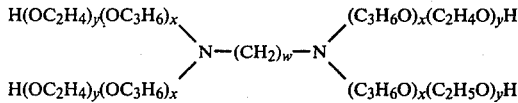

wherein w is an integer of from 2 to 6 containing approximately 40% to 80% poly(oxyethylene) and approximately 20–60% poly(oxypropylene) and having a molecular weight of 7,000 to 50,000; and x and y are any integers within the above constraints; and b. a pharmacologically effective amount of drug selected from the group consisting of antibacterial substances, antihistamines and decongestants, antiinflammatories, antiparasitics, antivirals, local anesthetics, antifungal, amebecidal, or trichomonocidal agents, analgesics, antiarthritics, antiasthmatics, anticoagulants, anticonvulsants, antidepressants, antidiabetics, antineoplastics, antipsychotics, antihypertensives, muscle relaxants and antiprotozoals; and c. a pharmaceutically acceptable acid or base being in sufficient quantity to adjust the pH of the composition to range from 2 to 9 and wherein the composition is liquid at about room temperature or below.

29. A method of treatment according to claim 28 wherein the polymer is one wherein w is 2.

30. A method of treatment according to claim 23 wherein the polymer is Tetronic ®1307.

31. A method of treatment according to claim 28 wherein the gel-sol transition temperature of the composition is room temperature or below and said composition is liquid at this temperature.

32. A method of treatment of claim 28 wherein said pharmaceutical composition is administered rectally, urethrally, nasally, vaginally, otically or orally within the buccal pouch.

33. A method of treatment according to claim 28 wherein the antibacterial substances are selected from the group consisting of beta-lactam antibiotics, tetracyclines, chloroamphenicol, neomycin, gramicidin, bacitracin, sulfonamides, aminoglycoside antibiotics, tobramycin, nitrofurazone, nalidixic acid and analogs and the antimicrobial combination of fludalanine/pentizidone.

34. A method of treatment according to claim 28 wherein the antihistaminics and decongestants are selected from the group consisting of perilamine, chlorpheniramine, tetrahydrozaline and antazoline.

35. A method of treatment according to claim 28 wherein the anti-inflammatory drugs are selected from the group consisting of cortisone, hydrocortisone, betamethasone, dexamethasone, fluocortolone, prednisolone, triamcinalone, sulindac and its salts and corresponding sulfide.

36. A method of treatment of claim 28 wherein the antiparasitic compound is ivermectin.

37. A method of treatment according to claim 28 wherein the antiviral effective compounds are selected from the group consisting of acyclovir and interferon.

38. A method of treatment according to claim 28 wherein the local anesthetics are selected from the group consisting of benzocaine, lidocaine and procaine.

39. A method of treatment according to claim 28 wherein the antifungal, antiprotozoal, amebecidal or trichomonacidal agent is selected from the group consisting of polyoxyethylene nonylphenol, alkylaryl sulfonate, oxyquinoline sulfate, miconazole nitrate, sulfonilamide, condicidin, sulfisoxazole, nystatin, clotrimazole metronidazole, chloramphenicol, chloroquine, trimethoprim or sulfamethoxazole.

40. A method of treatment according to claim 28 wherein the analgesic drug is selected from the group consisting of diflunisal, aspirin or acetaminophen.

41. A method of treatment according to claim 28 wherein the antiarthritics are selected from the group consisting of phenylbutazone, indomethacin, sulindac and its salts and corresponding sulfide, dexamethasone, ibuprofen, allopurinol, oxyphenbutazone or probenecid.

42. A method of treatment according to claim 28 wherein the antiasthma drugs are selected from the group consisting of theophylline, ephedrine, beclomethasone diproprionate and epinephrine.

43. A method of treatment according to claim 28 wherein the anticoagulants are selected from the group consisting of heparin, bishydroxycoumarin, and warfarin.

44. A method of treatment according to claim 28 wherein the anticonvulsants are selected from the group consisting of diphenylhydantoin and diazepam.

45. A method of treatment according to claim 28 wherein the antidepressants are selected from the group consisting of amitriptyline, chlordiazepoxide perphenazine, protriptyline, imipramine and doxepin.

46. A method of treatment according to claim 28 wherein the antidiabetics are selected from the group consisting of insulin, tolbutamide, tolazamide, acetohexamide and chlorpropamide.

47. A method of treatment according to claim 28 wherein the antineoplastics are selected from the group consisting of adriamycin, flurouracil, methotrexate and asparaginase.

48. A method of treatment according to claim 28 wherein the antipsychotics are selected from the group consisting of prochlorperazine lithium carbonate, lithium citrate, thioridazine, molindone, fluphenazine, trifluoperazine, perphenazine, amitriptyline and triflupromazine.

49. A method of treatment according to claim 28 wherein the antihypertensives are selected from the group consisting of spironolactone, methyldopa, hydralazine, clonidine, chlorothiazide, deserpidine, timolol, propranolol, metoprolol, prazosin hydrochloride and reserpine.

50. A method of treatment according to claim 28 wherein the muscle relaxants are selected from the group consisting of melphalan, danbrolene, cyclobenzaprine, methocarbamol and diazepam.

51. A method of treatment according to claim 28 wherein the composition includes a buffering agent or salt of from 0% to 5% by weight of the composition.

52. A method of treatment according to claim 51 wherein the buffering agent or salt is selected from the group consisting of alkali or alkali earth carbonates, chlorides, sulfates, phosphates, bicarbonates, citrates, borates, acetates and succinates.

53. A method of treatment according to claim 28 wherein the composition includes from 0.001% to 5% by weight of the composition of a preservative.

54. A method of treatment according to claim 53 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

55. A method of treatment according to claim 28 wherein the acid or base is selected from the group consisting of hydrochloric acid or sodium hydroxide.

* * * * *

UNITED STATES PATENT AND TRADEMARK OFFICE
CERTIFICATE OF CORRECTION

PATENT NO. : 4,478,822

DATED : October 23, 1984

INVENTOR(S) : John L. Haslam; Takeru Higuchi and Arthur R. Mlodozeniec.

It is certified that error appears in the above—identified patent and that said Letters Patent is hereby corrected as shown below:

In Claim 1., column 7, line 40, "pourch" should read ---pouch---,
column 7, line 61, "amebecidal" should read---amebicidal---.

In Claim 11, column 8, line 37, "amebecidal" should read ---amebicidal---.

In Claim 28., column 9, line 41, "pourch" should read ---pouch---, line 61, "amebecidal" should read ---amebicidal---.

Signed and Sealed this

Seventh Day of May 1985

[SEAL]

Attest:

DONALD J. QUIGG

Attesting Officer     Acting Commissioner of Patents and Trademarks